United States Patent [19]
Petillo

[11] Patent Number: 6,099,536
[45] Date of Patent: *Aug. 8, 2000

[54] HYDRAULIC POWERED SURGICAL DEVICE

[75] Inventor: Phillip J. Petillo, Ocean, N.J.

[73] Assignee: Pacific Surgical Innovations, San Carlos, Calif.

[ * ] Notice: This patent issued on a continued prosecution application filed under 37 CFR 1.53(d), and is subject to the twenty year patent term provisions of 35 U.S.C. 154(a)(2).

[21] Appl. No.: 09/259,970

[22] Filed: Mar. 1, 1999

Related U.S. Application Data

[63] Continuation of application No. 08/681,182, Jul. 22, 1996, Pat. No. 5,876,410.

[51] Int. Cl.[7] ................................................... A61B 17/10
[52] U.S. Cl. ............................................ 606/142; 606/157
[58] Field of Search ..................................... 606/151, 157, 606/139, 142

[56] References Cited

U.S. PATENT DOCUMENTS

| 4,976,722 | 12/1990 | Failla ........................................ 606/157 |
| 5,171,252 | 12/1992 | Friedland ................................. 606/151 |
| 5,713,911 | 2/1998 | Racenet et al. ......................... 606/157 |

OTHER PUBLICATIONS

3 Photographs of Clip Applier Apr. 10, 1994.

*Primary Examiner*—Michael Buiz
*Assistant Examiner*—David O. Reip
*Attorney, Agent, or Firm*—C. Richard Eby

[57] ABSTRACT

A hydraulically powered surgical device (20) includes a surgical instrument (24) having a tool (36) is mounted to one end of a handle (26). A hydraulic actuator (62) is mounted to the opposite end of the handle (26) and is also operatively connected to the tool (36). A source of hydraulic pressure includes a fluid reservoir (46) mounted with respect to an actuating element (21). The actuating element (21) is used to selectively apply a hydraulic pressure to the hydraulic actuator (62), thereby operating the tool (36).

8 Claims, 4 Drawing Sheets

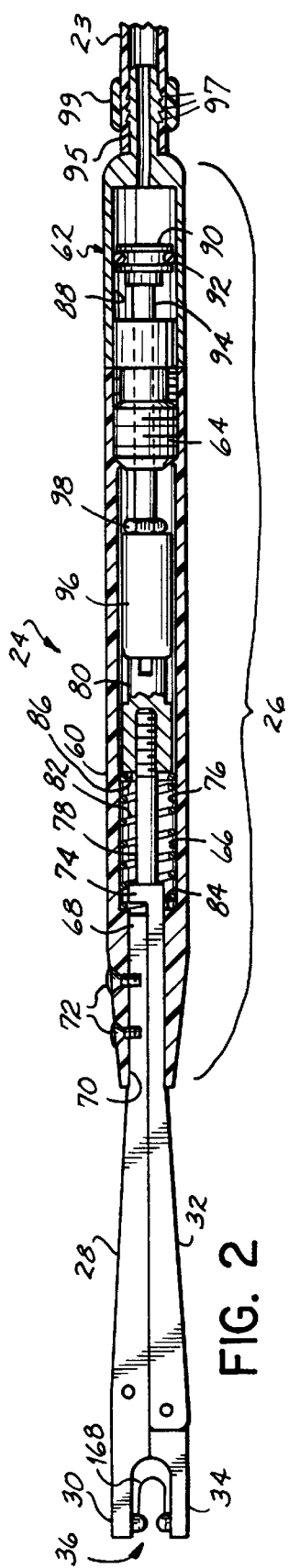
FIG. 2
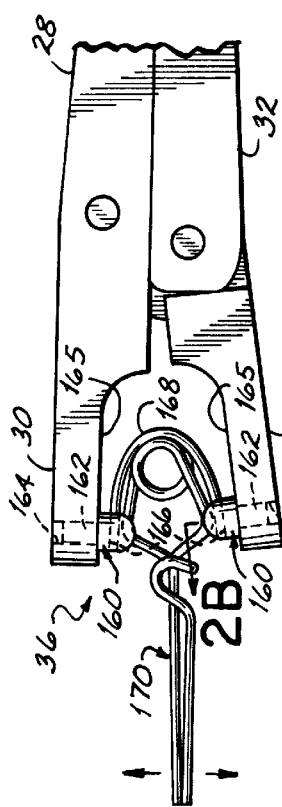
FIG. 2A
FIG. 2B
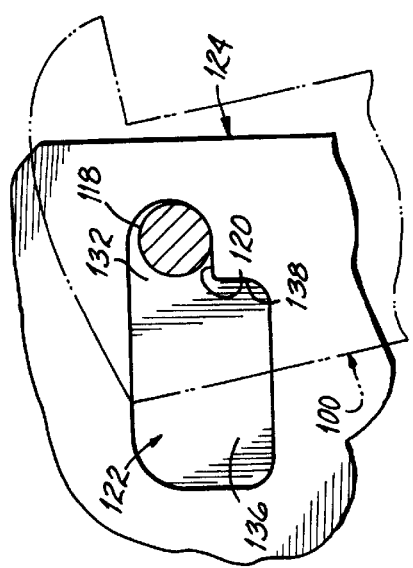
FIG. 3A
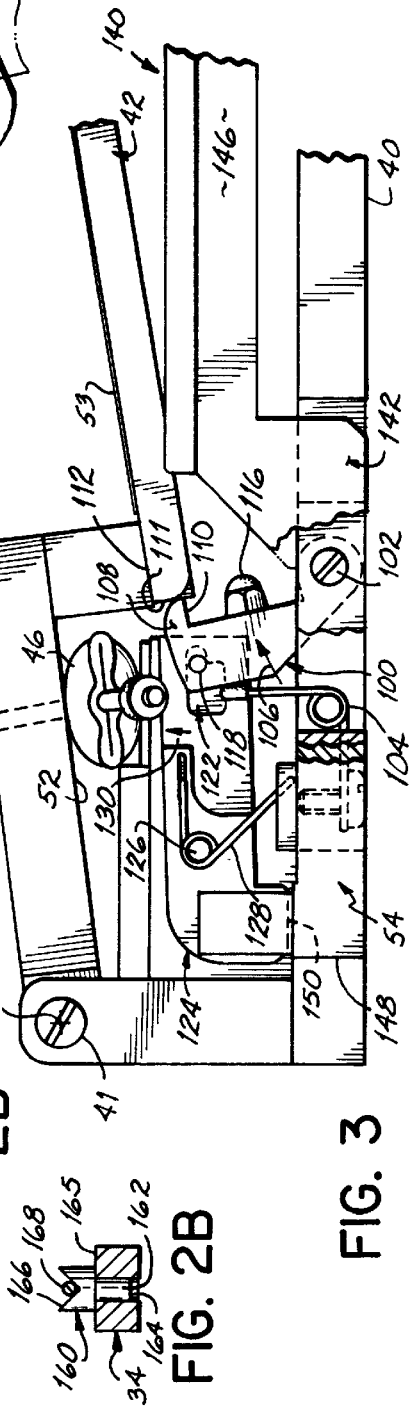
FIG. 3

HYDRAULIC POWERED SURGICAL DEVICE

This application is a continuation of Ser. No. 08/681,182 filed Jul. 22, 1996 now U.S. Pat. No. 5,876,410.

FIELD OF THE INVENTION

This invention relates generally to surgical instruments and more particularly, to a surgical instrument for applying and removing a hemostatic clip on a blood vessel.

BACKGROUND OF THE INVENTION

Hemostatic clips, including aneurysm clips, are applied to blood vessels in various ways to close or strengthen a blood vessel during or after surgery. Normally, forceps are used to place or apply the clips. Forceps of the type often used are described in U.S. Pat. No. 5,104,397. Such forceps have a pair of scissors-like arms. The longer portion of the arms or handles are located on one side of the pivot and are adapted to fit into and be operated by the surgeon's hand. The arms of the forceps include a spring therebetween for biasing the gripping end of the forceps toward an open position. The forceps further include a latching device that holds the arms in different positions corresponding to the open and closed states of the hemostatic clip.

The above type of hemostat or forceps, while functioning satisfactorily, have certain characteristics which present different problems during the procedure. For example, the handle portion of the forceps are generally designed to be gripped between the thumb and forefinger and have a spread of three centimeters or more. The relatively wide spread handles of the forceps makes them difficult to rotate or turn with the fingers. Another disadvantage of that design is that the forceps have a tendency to obscure the surgeon's view of the site where the clip is to be applied. Further, the surgeon's hand first accurately positions and orients the forceps and clip with respect to the vessel. Next, the surgeon must, with a further hand motion, actuate the forceps to open and then close the clip on the vessel without changing the position or orientation of the clip. Obviously, the above is a time-consuming, delicate process which prolongs the surgery. Further, repeated operation, that is, opening and closing, of the clip applier causes muscle stress and fatigue and is very demanding of the surgeon.

To overcome the above disadvantages, a powered surgical device is disclosed in U.S. Pat. No. 5,258,007 in which two parallel arms are connected at one end to form a gripper and are operatively coupled at their opposite end to an electric motor. One arm is connected at a distal end to a movable jaw of the gripper, and its other end is connected to a nut that is threadedly engaged to a screw on the output shaft of an electric motor. Therefore, rotation of the motor will cause a translation of the nut, the movable arm, and the movable jaw. The electric motor is controlled by a pair of foot pedals, one for opening the jaw, and the other for closing the jaw. With the jaws in an open position, a hemostatic clip is placed between the jaws, and the "close" foot pedal is used to control a closing of the gripper to a first position which holds the clip in the handle. The clip can then be oriented at different angles with respect to the end of the handle. By further actuating the "close" foot pedal, the jaws are brought more closely together in order to open the clip. After the clip is positioned over the vessel, the "open" foot pedal is depressed, which opens the jaws and permits the clip to close around the vessel. While the above device addresses some of the problems presented by the more traditional forceps design, certain problems remain, and in addition, new problems are introduced.

With the electric motor in the handle of the instrument, the handle is again approximately three centimeters in diameter and relatively awkward to rotate with the fingertips. Further, the bulk of the handle is greater than the earlier scissors-type forceps, and it also has the disadvantage of potentially obstructing the visibility of the surgeon during the procedure. The electric motor extends over approximately one-third the length of the instrument and provides a significant weight at the handle end of the instrument. The heavy weight of the motor at the handle end of the instrument is not offset by the relatively small jaws at the other end of the instrument; and therefore, the instrument has a disadvantage of being unbalanced which also makes it difficult to manipulate with the fingers. In addition, the weight of the motor makes the instrument substantially heavier than the mechanical forceps it is designed to replace. The heavier weight makes it more difficult to hold steadily over time, and in longer procedures, is more demanding and tiring on the surgeon than the prior mechanical forceps.

In addition to certain disadvantages resulting from its size and weight, the electric clip applier has other disadvantages in its operation. For example, after a surgeon has carefully and accurately positioned the clip, operating the motor with a foot pedal will cause the rotor, the motor output shaft and the threaded screw to angularly accelerate. That angular acceleration will cause a slight twisting moment of the instrument, which the surgeon must overcome by bucking the torque. If that fails, the surgeon will have to reorient the clip with respect to the vessel. Further, the rotating inertia of the motor rotor, its output shaft and threaded screw results in the motor continuing to rotate through a small angle after power has been removed. That overrun causes the movable jaw to overshoot slightly from the desired position observed by the surgeon when the foot pedal was released. Consequently, in some situations, the surgeon may be required to oscillate the motor back and forth until the exact final position of the movable jaw of the gripper is achieved.

In its preferred embodiment, the electric clip applier requires the use of two foot pedals, one to open the jaws, and a second to close the jaws. It is extremely difficult for a surgeon in a standing posture to manipulate the two foot switches as implemented. It has been suggested that the device be operated by the surgeon sitting in a chair specially designed to elevate the surgeon to the desired height for the operation and having the foot pedals attached thereto. Obviously, such an arrangement severely limits the flexibility of the surgeon's motion with respect to the surgical procedure. In addition, there are other concerns and disadvantages with the use of an electric powered applier, for example, the potential problems of a power loss, intermittent power, a clutch failure, etc. The problem of a power loss is especially acute if the power loss occurs when the clip is partially applied or applied but not released. A further disadvantage is that the electric powered clip applier is substantially more costly and expensive than the manual forceps that it replaces.

Therefore there is a need for a powered clip applier that is smaller in size, lighter in weight, does not create torque on the instrument in its operation and does not require connection to hospital utilities.

SUMMARY OF THE INVENTION

The present invention provides a hydraulically powered surgical device that is small in size, lightweight, torque-free in operation, highly responsive to user actuation and has an independent self contained source of power. More specifically, the hydraulically powered surgical device of the present invention is easier to use than the prior manual and electric-powered devices and is not subject to power loss within a hospital. It has a high degree of flexibility and is less stressful and less tiring to use by the surgeon.

In accordance with the principles of the present invention, a hydraulically powered surgical device includes a surgical instrument to which a tool is mounted. A hydraulic actuator is also mounted to the surgical instrument and is operatively connected to the tool. A source of hydraulic pressure is located remote from the surgical instrument and is fluidly connected to the hydraulic actuator. The source of hydraulic pressure is selectively actuated to supply a hydraulic pressure to the hydraulic actuator, thereby operating the tool.

In one aspect of the invention, the hydraulic powered surgical instrument is a hemostatic clip applier, and the tool is a gripper having pivotally moving jaws. The jaws have inner directed opposed surfaces that move toward and away from each other. A clip support is mounted on each of the inner surfaces of the jaws and each support has a groove adapted to receive one side of the clip. The clip holder further includes a support element extending between common ends of the groove to block motion of the hemostatic clip in one direction within the grooves.

In another aspect of the invention, a sensor is operatively connected to the hydraulic actuator for detecting forces applied by the hydraulic actuator to the tool. The sensor includes a display for providing a representation of the detected forces.

These and other objects and advantages of the present invention will become more readily apparent during the following detailed description taken in conjunction with the drawings herein.

BRIEF DESCRIPTION OF THE DRAWINGS

FIG. 2 is a cross-sectional view of a hemostatic clip applier in accordance with the principles of the present invention.

FIG. 2A is an enlarged view of the gripper illustrating the clip support.

FIG. 2B is a cross-section taken along line 2B—2B in FIG. 2.

FIG. 3 is a partial side elevation view of the latch mechanism of the actuating element in its ready position.

FIG. 3A is an enlarged view of the latch pin and first rocker arm slot.

DETAILED DESCRIPTION OF THE INVENTION

Figure 1:
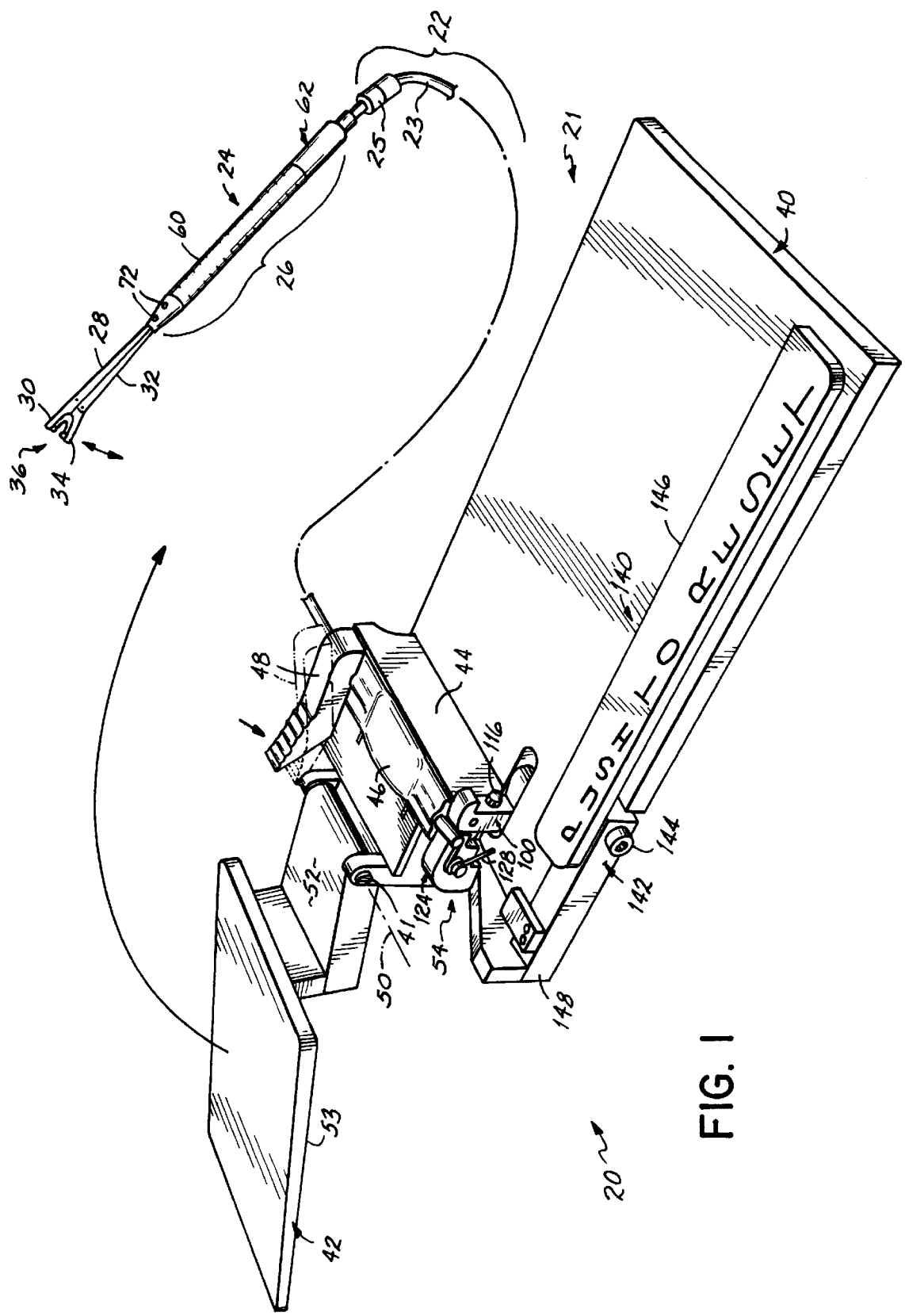
FIG. 1 is a perspective view of a hydraulic powered surgical device in accordance with the principles of the present invention.

Referring to FIG. 1, a hydraulic powered surgical device 20 is comprised a control or actuating device 21 and an associated hydraulic power supply 22. The hydraulic power supply 22 is hydraulically connected by tubing 23, with a hydraulically powered surgical instrument, for example, the hemostatic clip applier 24. A swivel coupling 25 prevents the tubing 23 from twisting when the clip applier 24 is turned and manipulated. The clip applier 24 has a handle 26 connected to one end of a static arm 28 that, in turn, has an implement, for example, a fixed jaw 30 connected to the distal end of the static arm 28. A movable arm 32 has a distal end extending from the handle 26, and an another implement, for example, operating or movable jaw 34 is pivotally connected to the distal ends of both arms 28, 32. In response to operation of the actuating element 21, the hydraulic power supply 22 causes the movable arm 32 to translate with respect to the fixed arm 28, thereby pivoting the movable jaw 34 toward and away from the fixed jaw 30. The pivoting motion of the movable jaw 34, with respect to the fixed jaw 30, permits the jaws to function as a gripping tool 36 to selectively grip, open, close, and release a hemostatic clip that is located between the jaws 30, 34.

The actuating device 21 has a base 40 and a lever or pedal 42 hinged with respect to a pivot pin 41 at one end of the base 40. The base 40 includes a pad or block 44 for supporting a hydraulic fluid or liquid reservoir 46 of the hydraulic power supply 22 that provides a source of fluid pressure. The liquid reservoir 46 is preferably made from a pliable plastic tube that is filled with mineral oil and is connected at one end to the tubing 23, which has its other end connected to the clip applier 24 via swivel coupling 45. The reservoir tube 46 is placed on the block 44 and is held in place by a manually operable spring biased clip 48. The lever 42 is then pivoted about pivot pin 41, providing an axis of rotation 50, so that the bearing surface 52 contacts the upper surface of the tube 46; and the pedal 42 extends over the base 40. The pedal 42 has surface 53 adapted to receive the foot of a user, so that depressing the pedal 42, that is, moving it in a generally downward direction, compresses the reservoir tube 42. Compressing the tube 46 applies a hydraulic pressure to the clip applier 24, thereby translating the movable arm 32 outwardly and moving the movable jaw 34 toward a closed position, thereby closing the gripper 36. Reducing the force applied to the pedal 42, that is, lifting the foot therefrom, permits the hydraulic reservoir tube 46 to decompress and reduces the hydraulic pressure being applied to the clip applier 24. The movable arm 32 translates inwardly toward the handle 26; and, in turn, the movable jaw 34 of the gripper 36 to returns toward its open position. The actuating device 21 further includes a latch mechanism 54 that operates to hold the pedal 42 in a position applying a desired hydraulic pressure to the clip applier 24, thereby holding the gripper 36 closed. The latch mechanism 54 can selectively be inhibited and then reset in accordance with the desired operation of the gripper 36.

FIG. 2 illustrates the clip applier instrument 24 in more detail. The handle 26 is preferably constructed of two pieces, a tubular forward handle 60 and a hydraulic actuator 62 forming a rearward endpiece of the handle 26. The fluid cylinder 62 is part of the hydraulic power supply 22 and connected to the forward handle component 60 by threads 64. The tubular component has a multiple diameter longitudinal bore 66 extending longitudinally and centrally therethrough. The static arm 28 has one end 68 extending through a smaller diameter portion 70 of the bore 66 and is connected to the tubular forward handle 60 by fasteners preferably screws 72. One end 74 of the movable arm 32 also extends through the smaller bore 70 and into a larger diameter portion 76 of the bore 66. The one end 74 of the movable arm 32 has a threaded rod 78 extending therefrom and onto which a nut 80 is connected. A movable arm return spring 82 is mounted between a shoulder 84 connecting the bores 70, 76 and is also captured by an end face 86 of the nut 80. The return spring 82 biases the nut 80, threaded rod 78, movable arm 32, and movable jaw 34 to a position at which the jaw 34 is in its open position. When there is no hydraulic pressure being applied to the instrument 24, the lock open position of the movable jaw is determined by the distal end of the movable arm blocking motion of the movable jaw 34 in the opening direction.

The end piece 62 of the handle 26 functioning as a fluid actuator such as a cylinder has an internal bore 88 that receives hydraulic fluid from the reservoir 46 (FIG. 1) via tubing 23. A piston 90 is slidingly mounted within the cylinder 88 and has sealing ring 92 to prevent leakage of the hydraulic fluid past the piston 90. A rod 94 has one end fixed to the piston 90 and has a distal end extending from the end piece or cylinder 62. An actuating shaft 96 is threaded along with the rod 94 and secured by a lock nut 98. The position of the movable jaw 34 with respect to the fixed jaw 30 can be adjusted by changing the location of the actuating shaft 96 on the piston rod 94. Therefore, the relative position of the jaws 34 can be adjusted to a desired position to accept and hold a clip prior to the clip being opened.

The end piece 62 of the handle 26 has a standard barbed fitting 95 with rings 97 extending therefrom. The tubing 23 is first slid over the barb fitting 95 in the standard manner, and then a collar or sleeve 99 is forcibly slid over the tubing 23 and the fitting 95 to secure the tubing 23 on the fitting 95. Preferably, the collar 99 has an internal diameter that is approximately 0.007 inches smaller than the diameter of the tubing 23 after it has been placed over the fitting 95. The internal diameter of the collar 99 may vary and will depend on the diameter of the barb fitting 95, the wall thickness of the tubing 23, the tubing material, etc. The collar can be made from "DELRIN", "NYLON" or "ABS" plastic material, polyvinylchloride, stainless steel, aluminum or other material depending on the application. The collar provides a fluid tight tubing clamp that does not have protruding ears, crimp connections, screws, etc. that may interfere with the surgeon's hand or tear the surgeon's glove.

Referring to FIG. 3, the gripper 36 is maintained in its closed position by a latching mechanism 54 that includes a latch 100 that is pivotally connected to the base 40 at 102. A spring 104 is connected between the latch 100 and the base 40. The spring 104 biases the latch 100 in the direction of the arrow 106, which is to the right as viewed in FIG. 3. The latch includes a projection or hook 108 forming a shoulder on a lower surface 110. As the lever or pedal 42 is pushed downward and pivots with respect to the pivot pin 41, the edge 111 of the pedal 42, slides over the hook 108 until the upper latch surface 112 of the pedal 42 moves to a position that is below the surface 110. At that point, the spring 104 pushes the latch 100 to the right, thereby pushing the surface 110 of the hook 108 over the surface 112 of the pedal and catching or holding the pedal in that position.

Referring to FIGS. 3 and 3A, during the motion of the pedal 42 to the latched position, a cam follower pin 118 extending from a side surface of the latch 100 moves along a surface 120 of a cam slot 122. The cam slot is located in one end of a first rocker arm 124 that is pivotally mounted intermediate its ends on a pivot pin 126. A spring 128 is connected between the rocker arm 124 and the base 40 to bias the one end of the first rocker arm 124 in a generally upward direction as indicated by the direction arrow 130. The cam slot 122 is generally L-shaped with a substantially horizontal upper leg 132 that intersects a substantially vertical leg 136. During the motion of the pedal 42 and the latch 100 described with respect to FIGS. 3 and 3A, the cam follower pin 118 rides along the surface 120 of the horizontal leg 132.

Figure 4:
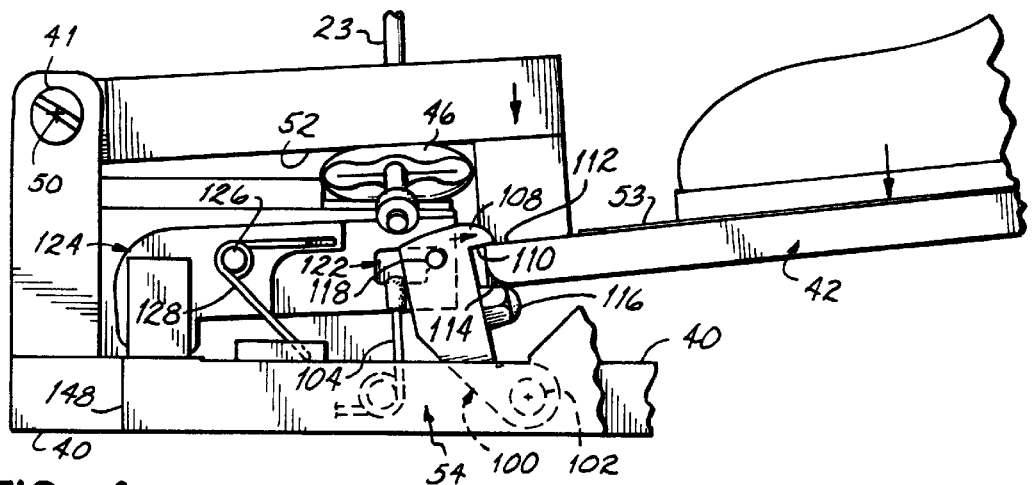
FIG. 4 is a partial side elevation view of the latch mechanism of the actuating element in its latched position.
Figure 5:
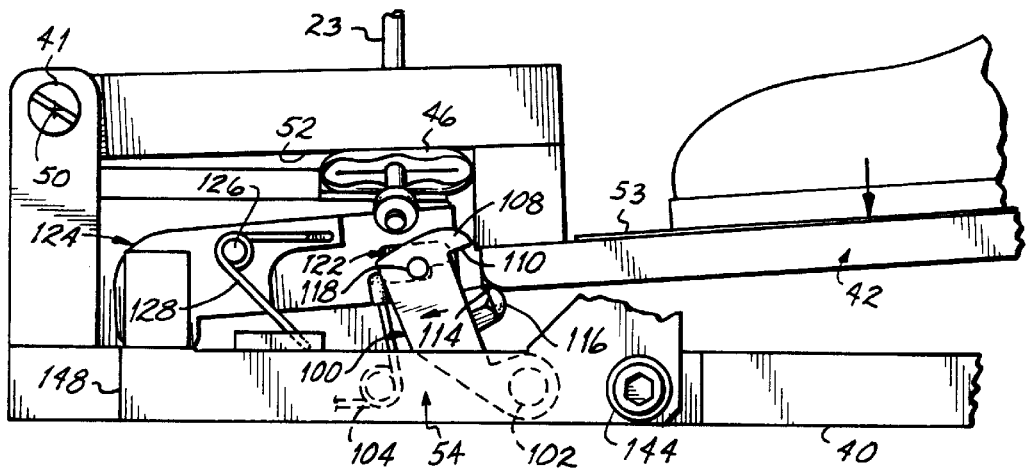
FIG. 5 is a partial side elevation view of the latch mechanism of the actuating element illustrated in its retracted position.

The latched position of the pedal 42 is illustrated in FIG. 4. The system is designed such that when the pedal 42 is in the latched position, the hydraulic pressure provided by the compressed reservoir 46 causes the movable jaw 34 of the gripper 36 to pivot to its closed position. Further depression of the pedal 42 causes it to move further downward until a lower corner edge 114 contacts the release block 116. Continued downward motion of the pedal 42 causes the corner edge 114 to push the release block 116, the latch 100, and the cam follower pin 118 to the left as viewed in FIG. 4. Those motions continue until the action of the corner edge 114 of the pedal 42 on the release block 116 pushes the cam follower pin 118 off of the cam surface 120 and into the vertical slot 136. At that time, the spring 128 biases that end of the first rocker arm upward, moving the vertical slot 136 past the pin 118 as illustrated in FIG. 5. The bias of spring 104 causes the pin 118 to slide along the generally vertical surface 138 of the vertical slot 136.

When the pin 118 is in the vertical slot 136, the latch 100 is moved to its retracted position, and the lower surface 110 of the hook 108 is disengaged from the upper latch surface 112 of the pedal 42. Consequently, the pedal 42 is unlatched; and as the downward force is removed from the pedal, the hydraulic forces within the reservoir 46 and the return spring 82 (FIG. 2) push the reservoir back to its uncompressed state and, in turn, lift the pedal 42 to its rest position illustrated in FIG. 6. With the latch 100 in its retracted position, the pedal 42 may be depressed and released to respectively close and open the gripper 36 independent of the latch 100. The operation of the latch is thus inhibited and will not interfere with the operation of the pedal 42 and the gripper 36.

Figure 6:
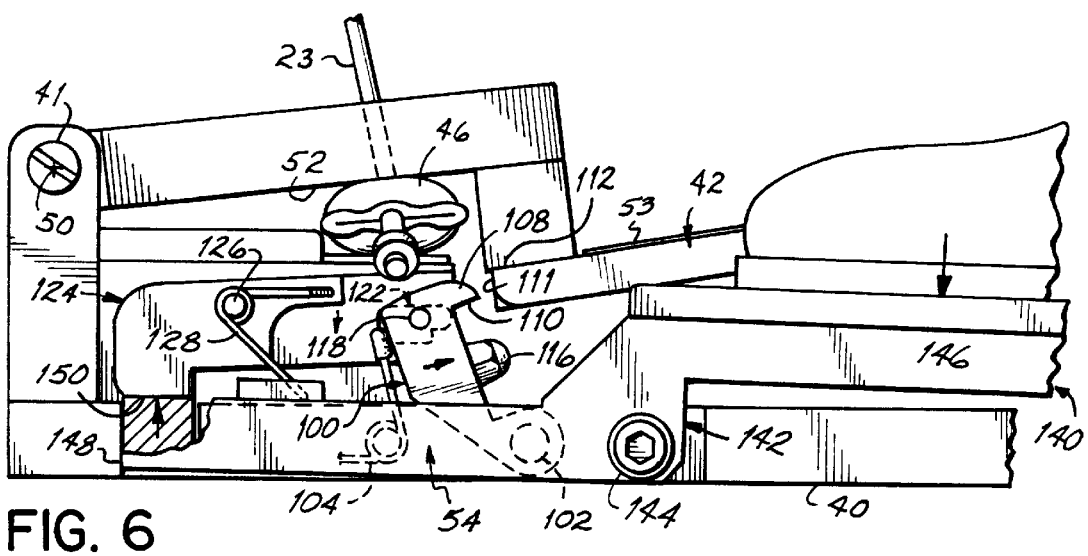
FIG. 6 is a partial side elevation view of the position of the first rocker arm as set by the reset pedal.

The latch 100 can be reset so that is again responsive to the motion of the pedal 42 by actuating the reset element 140, which includes a second rocker arm 142 pivotally mounted to the base 40 on pivot pin 144. The latch 100 is reset by depressing the first end 146 of the second rocker arm 142 downward. That action pivots the opposite end 148 of the second rocker arm 142 in an upward direction. The second end 148 of the second rocker arm 142 contacts the other end 150 of the first rocker arm 124. Further downward motion of the first end 146 of the rocker arm 142 moves the opposite end 150 of the first rocker arm 124 generally upward, thereby pivoting the first rocker arm 124 about its pivot pin 126 and against the bias of the spring 128. That motion moves the vertical slot 136 downward with respect to the cam follower pin 118 until the cam follower pin 118 loses contact with the surface 138 and enters the horizontal slot 132 as shown in FIG. 6. At that point, the spring 104 pivots the latch 100 about its pivot pin 102 to the right as illustrated in FIG. 5 until the latch 100 reaches the starting or active position illustrated in FIG. 3.

In use, hemostatic clips have different configurations because they are designed to serve different purposes, for example, such clips may be designed to pinch off aneurysms. Further, each type of hemostatic clip is also manufactured in different sizes. Therefore, the gripper 36 of the clip applier instrument 24 must be able to accommodate a wide variety of hemostatic clips. The arms 28, 32 and gripper jaws 30, 34 may be varied in their design to accept different styles and sizes of clips. Consequently, several clip applier instruments, as illustrated by the assembly of the forward handle body 60 in FIG. 2, can be made available to function with a single hydraulic power supply 22. Preferably, as described, the cylinder unit 62 (FIG. 2), tubing 23, and hydraulic fluid reservoir 46 are manufactured as a single unit. Therefore, different variations of the arms 28, 32 and jaws 30, 34 can be manufactured with the forward handle section 60 which in turn, can made to couple to a common cylinder and rearward handle section 62. Such variations include offsetting the arms 28, 32 for different procedures.

After the desired clip applier instrument 24 is chosen and coupled to cylinder 62 of the power supply 22, referring to FIGS. 2A and 2B, the appropriate clip holder specifically designed for the clip is inserted into the gripper 36. The clips of different suppliers are manufactured in different sizes with different wire of different diameters that is formed with different geometries. Further, the spring portion of the clip may vary in size and shape. Therefore, normally, the clip holder has clip supports 160 that are sized and shaped to receive and properly secure a particular clip. The clip supports 160 are preferably embodied by V-shaped grooves or slots 166. In order to permit the orientation of the clip to be varied, the grooves 166 are preferably disposed on the forward ends of support blocks or pins 162, and the opposite ends of the pins 162 are rotatably engaged in holes 164 in the opposed inner surfaces 165 of the jaws 30, 34.

An arcuate member 168 extends between one end of each V-groove 166 and functions to hold the grooves in a desired alignment, that is, a generally parallel relationship. The member 168 is preferably a flexible metal wire but may be made from any metallic or nonmetallic material that may be formed between the ends of the grooves 166. The member 168 helps to keep grooves 166 aligned regardless of their pivotal orientation to facilitate locating and inserting a clip 170 into the grooves 166. The arcuate member 168 also functions as a clip stop, and the sides of a clip 170 are inserted into the grooves 166 until a rear portion of the clip rests against the member 168. The clip supports 160 and arcuate member 168 are designed so that the clip 170 is initially held upon insertion in the supports 160 and will not fall out. Preferably, the clip 170 is initially secured in the supports 160 without any operation of the actuating element 21. Further, the clip must be held so that as the movable jaw 34 of the gripper 36 is closed, the clip 170 does not pop out of the supports 160.

When loaded in place, the clip 170, clip supports 160, and stop wire 168 may be rotated in the gripper 136 to a desired orientation. When in that position, the surgeon then presses the pedal 42 downward until the latch 100 latches the pedal in its first position, which closes the gripper 36 and opens the clip 170. The clip 170 and the end of the clip applier 24 is then inserted into the incision and then manipulated to a desired position with respect to the vessel or aneurysm. When in the desired position and orientation, the pedal 42 is depressed further until the release block 116 moves the latch back to its retracted position. The pedal 42 may then be released, and the return spring 82 in the clip applier 24, in combination with the decompression of the fluid reservoir 46, causes the gripper 36 to open, thereby closing the clip 170 on the desired vessel or aneurysm. Further release of the pedal 42 will continue to open the gripper 36 until the clip is released. The clip applier 24 may then be used to manipulate the clip and open or close the clip as desired by respectively depressing and releasing the pedal 42 without the latch 100 locking the pedal in place. When the surgeon desires to load another clip, the reset pedal 140 is depressed, thereby releasing the latch 100 from its retracted position so that it can again engage the pedal 42.

In other procedures, it may be desirable that the clip only be partially opened when it is moved into the incision. In that situation, referring to FIG. 2, the lock nut 98 is loosened, and the shaft 96 is rotated with respect to the rod 94 to move the shaft 96 to the right as viewed in FIG. 2. The lock nut 98 is then again tightened. With the shaft 96 in that new position, when a clip is placed in the clip supports, the clip may or may not be initially secured in the gripper. In either event, the surgeon then presses the pedal 42 downward until it latches in the first position, When in that position, the clip will be secured in the gripper 36 but will only be partially opened. Therefore, the clip presents a smaller profile and may more easily be moved into the incision than a fully open clip. The clip is then manipulated to a desired position with respect to the vessel or aneurysm. When in the desired position and orientation, the pedal 42 is depressed further until the release block 116 moves the latch back to its retracted position. Pressing the pedal 42 causes the clip to fully open, and the clip may then be placed over the vessel. The pedal 42 is then released; the gripper 36 opens; and the clip is released as described above. Therefore, by adjusting the position of the operating shaft 96 on the rod 94, the clip may be maintained closed or opened any desired amount when the pedal 42 is moved to the latched first position.

The above clip applier has many advantages, for example, not requiring the surgeon's hand to both position and orient the clip, as well as squeeze, pull or push an actuator in order to open and close the clip. Further, the clip applier instrument 24 is light, well-balanced and easy to rotate and manually manipulate. The hydraulic foot actuated power supply provides full responsiveness of the movable jaw to actions of the foot. The jaw 34 quickly and accurately follows the motion of the pedal 42; and therefore, the surgeon has full control over the acceleration, velocity and position of the movable jaw 34. Further, the small diameter of the clip applier 24 makes it easier for the surgeon to see over and around the clip applier into the surgical field. The applier and its gripper with the clip holder can easily accommodate different styles and clips. The applier 20 operates silently without torque or overshoot of the jaw 34. If there is any failure of the fluid power supply, the end cylinder 62 of the handle 26 can be quickly disassembled; and the hydraulic reservoir quickly removed from the actuating unit 21. A new reservoir can be installed, and a new cylinder 62 coupled to the clip applier instrument 24 in less than a minute.

Figure 7:
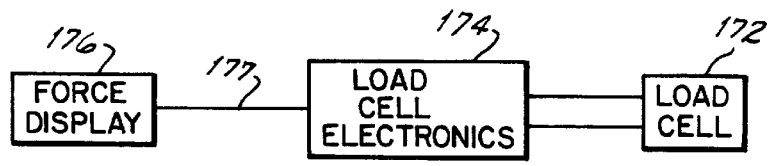
FIG. 7 is a schematic block diagram of an alternative embodiment of the invention using a load cell.

Referring to FIG. 7, an alternative embodiment of the invention uses a load cell 172 which is electrically connected to load cell electronics 174 that in turn provide an output signal that is utilized by a force display 176. The load cell 172 is preferably a force or torque sensor that is relatively small and capable of functioning in a surgical environment. For example, the sensor must be able to withstand sterilization in an autoclave unit. Load cells having those characteristics are commercially available in a wide range of shapes and sizes from Transducer Techniques of Temucula, Calif. The load cell electronics 174 normally will include a power source of, for example, a battery, and other electronics necessary to provide the desired output signal on line 177 to a display unit 176. The display unit may be a simple LED or LCD numerical display or may be a video display integrated in a microprocessor based unit to provide a graphics and/or numerical display of the forces measured by the load cell.

Referring to FIG. 2, the load cell may be integrated within any one of several components of the clip applier instrument 24. For example, the load cell may be integrated into one or more of the following elements: the rod 94, the actuating shaft 96, the lock nut 80, the threaded rod 78, the one end 74 of the movable arm 32 or the movable jaw 34. Alternatively, referring to FIG. 1, the load cell may be integrated into either the tubing 23, the bearing surface 52 of the pedal 42 or the upper surface of the block 44, so that the load cell is able to respond to the forces applied on the pedal 42 against the hydraulic reservoir 46.

In use, the force display 176 provides a representation of the force being applied against the movable jaw 34. The display can be used to check the forces required to open an aneurism clip. Normally, the clip is resilient in that the force required to open the clip can be correlated to the clamping force that the closed clip will apply around the aneurism. Therefore, by monitoring the force required to open the clip with the load cell, a defective clip may be detected.

Figure 8:
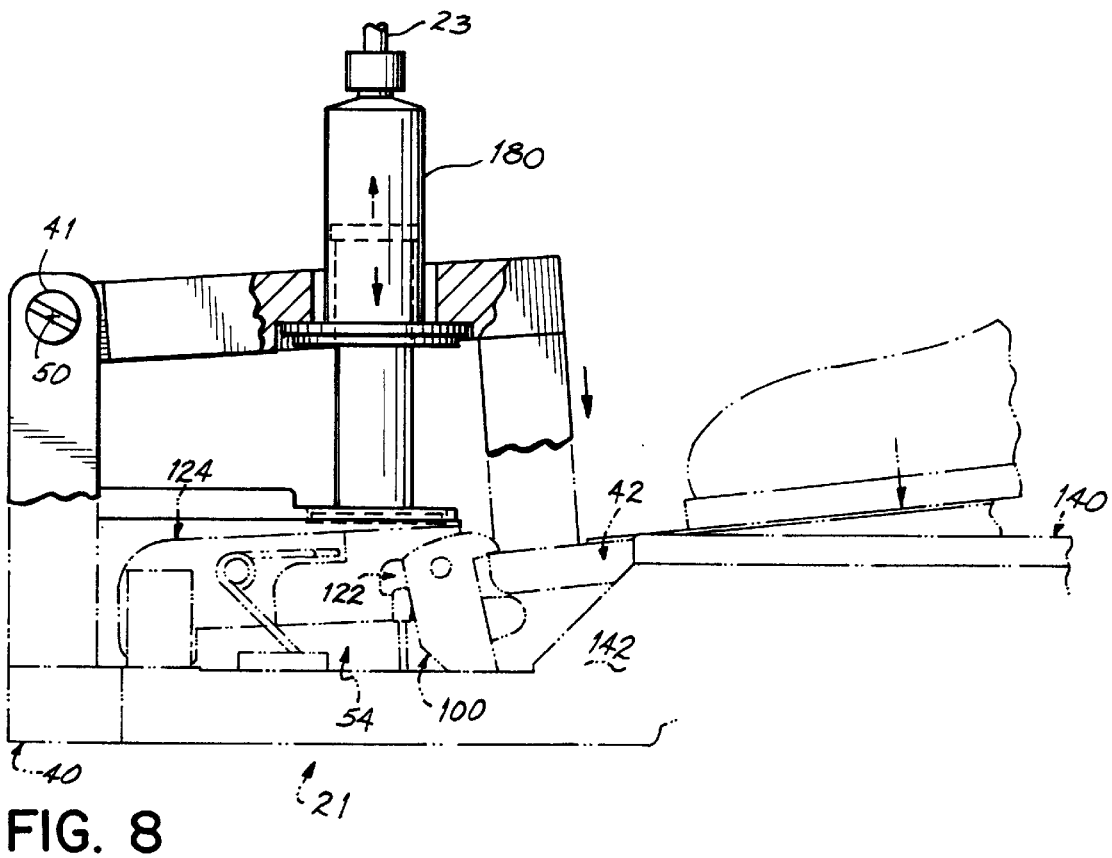
FIG. 8 is a partial side view of an alternative embodiment of the hydraulic power supply in accordance with the principles of the present invention.

While the invention has been set forth by a description of the preferred embodiment in considerable detail, it is not intended to restrict or in any way limit the claims to such detail. Additional advantages and modifications will readily appear to those who are skilled in the art. For example, referring to FIG. 8, the hydraulic reservoir may take the form of a syringe 180 which is actuated by the foot pedal. Further, the gripper 36 may be designed to open in response to actuating of the foot pedal and closed in response to release of the foot pedal. Alternatively, the gripper 36 may be designed to have two opposing movable jaws that are operated with or without a compound linkage.

As will be appreciated, the disclosed hydraulically powered surgical device has great versatility, and the hydraulically powered instrument 24 can be modified to accept and operate a great number of different tools, for example, retractor blades, needle holder blades, scissors, a bipolar, tweezers, forceps, punches, rongeurs, specula, shears, suction tubes, mirrors, dissectors, hooks, fiber optic cables, lights sources, clamps, hemostats tools for the infusion or aspiration of fluids and other microsurgical tools.

Further, while the hydraulic cylinder and rod are disclosed as providing a translating cylinder rod motion, cylinders may be used that produce a pivoting or rotating cylinder rod motion. Alternatively, a rack and pinion may be used with the translating cylinder rod to produce a pivoting motion. Further, in the disclosed embodiment, the hydraulic power supply is actuated with a user's foot, however, in the context of the invention, any manual actuation can be used to operate the hydraulic power supply, that is, a user's hand, finger, foot, etc. In addition, the lever of the pedal could be replaced by a manually actuated vice type of device as well a scissors or pliers type of device. Further, hydraulic reservoir 46 may be squeezed by a powered device, for example, a motorized vice or other motorized gripper device.

The pins 162 having the clip supports 160 may be rigidly mounted with respect to the jaws 30, 34. In addition the clip supports 160 may be formed directly on the jaws 30, 34 so that the pins 162 are not required.

The invention, therefore, in its broadest aspects is not limited to the specific detail shown and described. Consequently, departure may be made from the details described herein without departing from the spirit and scope of the claims which follow.

What is claimed is:

1. A clip support for a hemostatic clip for use with a gripper of a clip applier, the gripper having first and second pivoting jaws, each of the jaws having inner directed surfaces moving toward each other, the clip support comprising:

a pair of support blocks, each of the support blocks having one end adapted to be pivotally located with respect to the inner directed surface of one of the jaws, the support blocks having grooves on opposite ends extending substantially perpendicularly to pivot axes of the support blocks and adapted to receive side elements of a hemostatic clip; and an arcuate wire-like member extending between the support blocks, the arcuate wire-like member having ends rigidly connected to the support blocks at a fixed orientation with respect to the grooves to maintain the support blocks in a desired orientation with respect to each other.

2. The clip support of claim 1 wherein the ends of the arcuate wire-like member extend in a direction generally parallel to the grooves in the support blocks.

3. The clip support of claim 1 wherein the arcuate wire-like member is a flexible wire.

4. The clip support of claim 1 wherein each end of the arcuate wire-like member is formed within the groove of one of the support blocks.

5. The clip support of claim 4 wherein the grooves are generally V-shaped.

6. The clip support of claim 5 wherein the support blocks are generally cylindrical pins.

7. The clip support of claim 6 wherein the arcuate member is generally U-shaped between the support blocks.

8. The clip support of claim 1 wherein the one end of each of the support blocks is cylindrical.

* * * * *